United States Patent
Banju et al.

(10) Patent No.: US 7,512,437 B2
(45) Date of Patent: Mar. 31, 2009

(54) THREE-DIMENSIONAL OBSERVATION SYSTEM

(75) Inventors: Kazuo Banju, Hachioji (JP); Masahiro Kudo, Hino (JP); Shingo Nogami, Machida (JP); Takahiro Kogasaka, Hachioji (JP); Kazuo Morita, Hachioji (JP); Masayuki Irie, Hachioji (JP)

(73) Assignee: Olympus Corporation, Tokyo (JP)

( * ) Notice: Subject to any disclaimer, the term of this patent is extended or adjusted under 35 U.S.C. 154(b) by 450 days.

(21) Appl. No.: 10/842,807

(22) Filed: May 11, 2004

(65) Prior Publication Data

US 2005/0001899 A1    Jan. 6, 2005

(30) Foreign Application Priority Data

May 13, 2003   (JP)   ............... 2003-135004

(51) Int. Cl.
 *A61B 6/00*   (2006.01)
 *G02B 21/22*   (2006.01)
 *G02B 27/22*   (2006.01)
(52) U.S. Cl. ............... 600/476; 359/377; 359/466
(58) Field of Classification Search ............... 600/407, 600/476, 111; 348/51; 351/222; 396/20, 396/324; 359/377, 466
See application file for complete search history.

(56) References Cited

U.S. PATENT DOCUMENTS

| | | | | |
|---|---|---|---|---|
| 5,712,732 A | * | 1/1998 | Street | 359/630 |
| 6,278,480 B1 | * | 8/2001 | Kurahashi et al. | 348/59 |
| 6,473,229 B2 | * | 10/2002 | Nakamura | 359/377 |
| 6,525,878 B1 | * | 2/2003 | Takahashi | 359/466 |

FOREIGN PATENT DOCUMENTS

JP   8-194172   7/1996

* cited by examiner

*Primary Examiner*—Eric F Winakur
*Assistant Examiner*—Michael T Rozanski
(74) *Attorney, Agent, or Firm*—Scully, Scott, Murphy & Presser, P.C.

(57) ABSTRACT

The three-dimensional observation system of the present invention comprises an image picking-up part which has a parallax with respect to the object of observation and captures two images of the object of observation, an image display part which respectively displays the two images of the object of observation captured by the image picking-up part, and an optical system which is used to guide the two images of the object of observation displayed by the image display part to respective position in front of the left and right eyes of the observer facing the object of observation, such that the parallax direction of the image picking-up part and the parallax direction of the observer coincide, thus causing a three-dimensional image to be displayed.

16 Claims, 14 Drawing Sheets

THREE-DIMENSIONAL OBSERVATION SYSTEM

CROSS-REFERENCE TO RELATED APPLICATION

This application claims benefits of Japanese Application No. 2003-135004 filed in Japan on May 13, the contents of which are incorporated by this reference.

BACKGROUND OF THE INVENTION

1. Field of the Invention

The present invention relates to a three-dimensional observation system which allows the three-dimensional viewing of observation sites inside body cavities by means of an endoscope.

2. Description of the Related Art

Three-dimensional observation systems which allow the observation of three-dimensional images by picking up two images that have a parallax, and respectively guiding these captured images to the left and right eyes of an observer, have been known in the past.

Such three-dimensional observation systems have also attracted attention in the medical field, and surgical procedures using so-called three-dimensional endoscopes, in which this technique is applied to an endoscope, are becoming more widespread.

Meanwhile, fine surgical manipulation skill is required in surgical procedures that are performed while picking up the image of an observation site by means of an endoscope inserted into a body cavity and observing this endoscopic image; however, in the case of surgical procedures using a three-dimensional endoscope, delicate treatments that depend on a high degree of manipulation skill can be performed with greater assurance than in cases where surgical procedures are performed while observing a conventional two-dimensional endoscopic image.

In such a three-dimensional observation system, three-dimensional observation is generally made possible using a binocular system by picking up two images that have a parallax with respect to the object of observation, and respectively guiding these two captured images to the left and right eyes of the observer.

For example, devices in which two images are alternately displayed on a monitor screen that displays captured images, and these images are observed via viewing glasses equipped with a liquid crystal shutter that is synchronized with the switching of this display, and devices in which the direction of polarization of two images is varied, and the images are viewed via polarized viewing glasses that have different polarization directions for the left and right eyes and the like are known as display devices used to guide two such images that have a parallax to the eyes of the observer.

Meanwhile, in surgical procedures using an endoscope, the operating surgeon performing the procedure must perform an extremely delicate surgical manipulation while observing the endoscopic image, and it is important to alleviate the fatigue felt by the operating surgeon in realizing this delicate surgical manipulation.

Generally, in surgical procedures using endoscopic images, the images captured by the endoscope are displayed on a monitor placed inside the operating room. The surgical procedure is performed while viewing the operating site on the endoscopic image displayed on this monitor, and the operating instrument operated by the operating surgeon himself. In this case, the operating surgeon must work while directing his body toward the operating site on the patient undergoing the surgical procedure, and directing only his face toward the monitor. As a result, the operating surgeon is forced to adopt an unreasonable posture, so that fatigue tends to occur. In order to prevent the occurrence of such fatigue, it is desirable that the operating surgeon be able to observe the monitor screen while directing his face toward the front (a direction in which the operating surgeon views the operating site while facing the patient).

Furthermore, in order to perform the surgical procedure smoothly in addition to alleviating fatigue of the operating surgeon, numerous persons cooperating in the surgical procedure such as assistants that assist in the surgical procedure, anesthesiologists, nurses and the like are also involved, and it is necessary to perform the operation with the cooperation of these various cooperating persons. Accordingly, it is important that the operating surgeon himself be able to ascertain the status of the cooperating persons that surround the operating surgeon, and it is also necessary that the cooperating persons be able to grasp the surgical procedure being performed by the operating surgeon.

However, in cases where the viewing glasses equipped with a liquid crystal shutter or polarized viewing glasses are used in a surgical procedure that is performed while viewing a three-dimensional image, the monitor that displays this image is usually disposed in a position that is apart from observers such as the operating surgeon, cooperating persons and the like inside the operating room, so that the observers must constantly turn their faces toward the monitor when observing the three-dimensional image. This forces the observers into a posture that causes fatigue. Furthermore, the operating surgeon must ascertain the status of surrounding cooperating persons via the polarized viewing glasses or viewing glasses equipped with a liquid crystal shutter, so that it is difficult for the operating surgeon himself to ascertain the status of surrounding persons, and so that it is also difficult for the surrounding cooperating persons to ascertain the status of the operating surgeon.

Furthermore, in cases where the image that is observed is a three-dimensional image, the fatigue of the operating surgeon is also affected by the direction of the parallax. For example, in the image pickup device used for three-dimensional observation, two images that have a parallax in a certain direction are respectively viewed by the left and right eyes of the operating surgeon, so that a three-dimensional image is recognized. However, in cases where the parallax direction of the three-dimensional image viewed by the operating surgeon and the parallax direction of the operating surgeon are different, it is difficult to grasp the positional relationship between the orientation of the three-dimensional image and the orientation of the surgical operating instrument operated by the operating surgeon himself. This may cause the operating surgeon to become confused; as a result, the operating surgeon may suffer from fatigue.

As a display device for three-dimensional captured images that alleviates such fatigue of the operating surgeon and makes it easy to grasp surrounding conditions, a head-mounted display device, which has a monitor that displays two captured images and in which an optical system that guides the images displayed on this monitor to the eyes of the observer, has also been proposed (for example, see Japanese Patent Application Laid-Open No. 8-194172).

This head-mounted display device is mounted on the head of the operating surgeon; furthermore, switching means that allow the passage of external light to the monitor that displays the captured images, or that cut off such external light, are provided, so that the operating surgeon can visually recognize both three-dimensional captured images and the surrounding conditions by a switching operation between the passage and blocking of external light using the switching means.

The present invention provides a three-dimensional observation system used to perform surgical procedures while observing three-dimensional images, which makes it possible to perform fine surgical procedures while alleviating fatigue of the operating surgeon, and which also allows other persons cooperating in the surgical procedure to confirm images on the monitor observed by the operating surgeon, and thus facilitates mutual understanding between the operating surgeon and persons cooperating in the surgical procedure.

SUMMARY OF THE INVENTION

Briefly, the three-dimensional observation system of the present invention comprises an image picking-up part which has a parallax with respect to the object of observation, and captures two images of the object of observation, an image display part which displays respectively the two images of the object of observation captured by this image picking-up part, and an optical system which is used to guide the two images of the object of observation displayed by the image display part to respective position in front of the left and right eyes of the observer facing the object of observation, so that the parallax direction of the image picking-up part and the parallax direction of the observer coincide, thus causing a three-dimensional image to be displayed.

Additional features and advantages of the invention will be set forth in the description which follows, and in part will be obvious from the description, or may be learned by practice of the invention. The features and advantages of the invention may be realized and obtained by means of the instrumentalities and combinations particularly pointed out hereinafter.

DESCRIPTION OF THE PREFERRED EMBODIMENTS

Embodiments of the present invention will be described below with reference to the attached figures.

Figure 1:
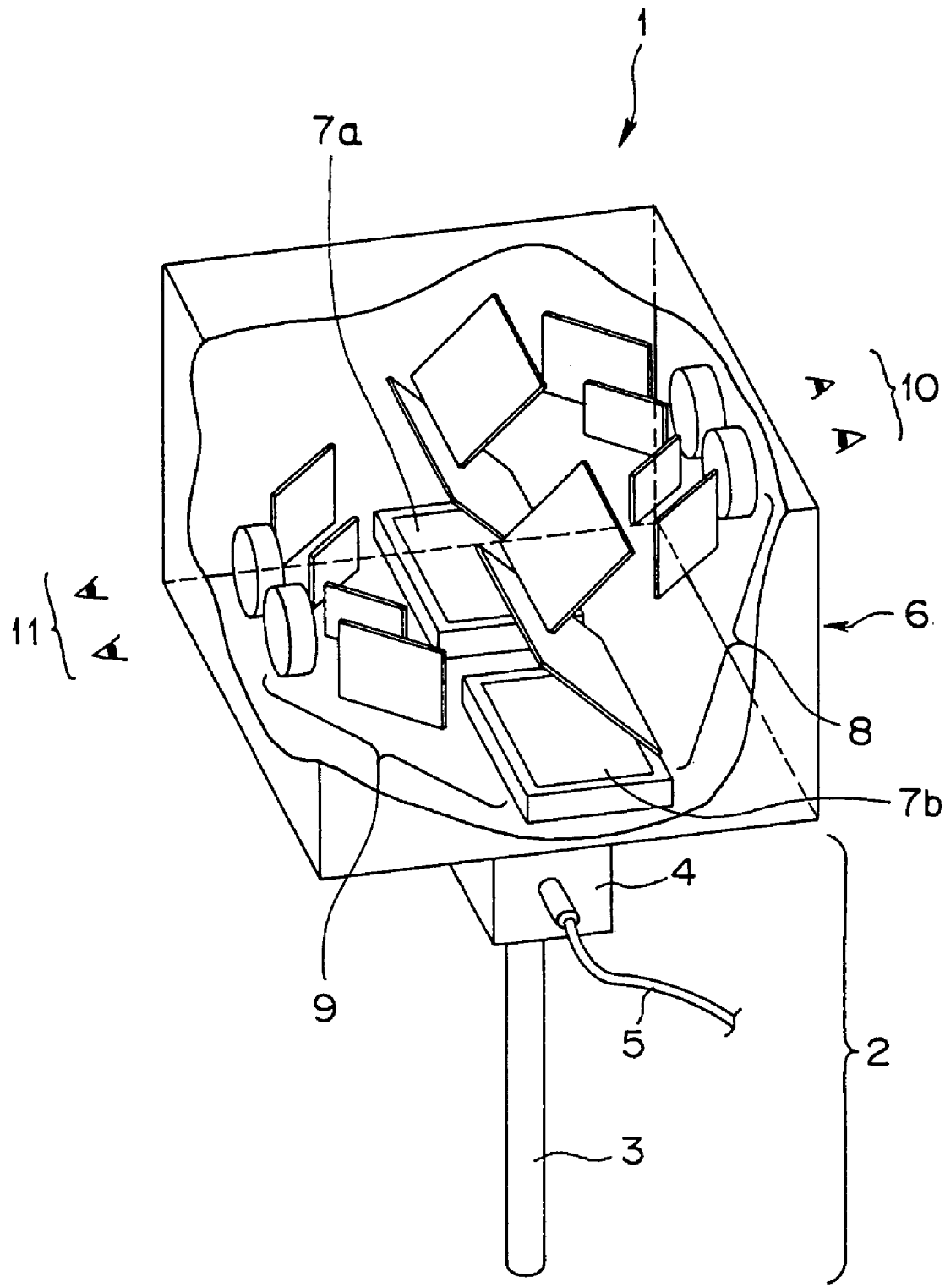
FIG. 1 is a perspective view which shows the overall construction of a three-dimensional observation system constituting a first embodiment of the present invention.
Figure 2:
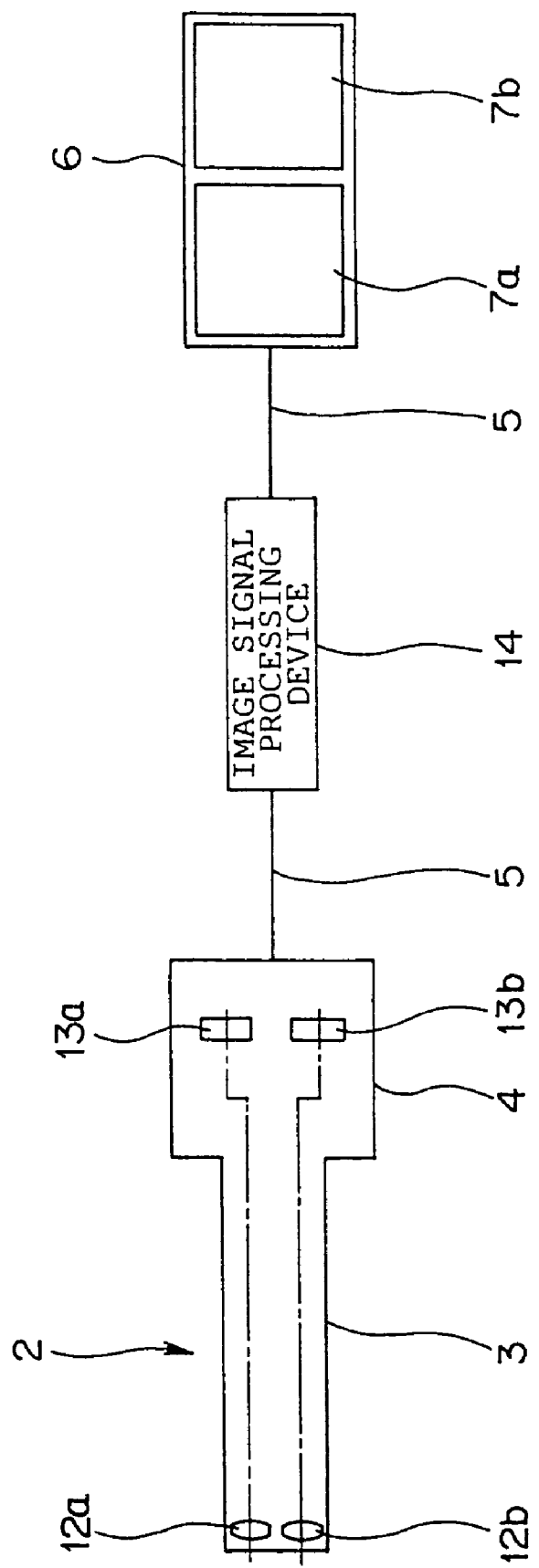
FIG. 2 is a block diagram which shows the schematic construction of the three-dimensional observation system of the first embodiment.
Figure 3:
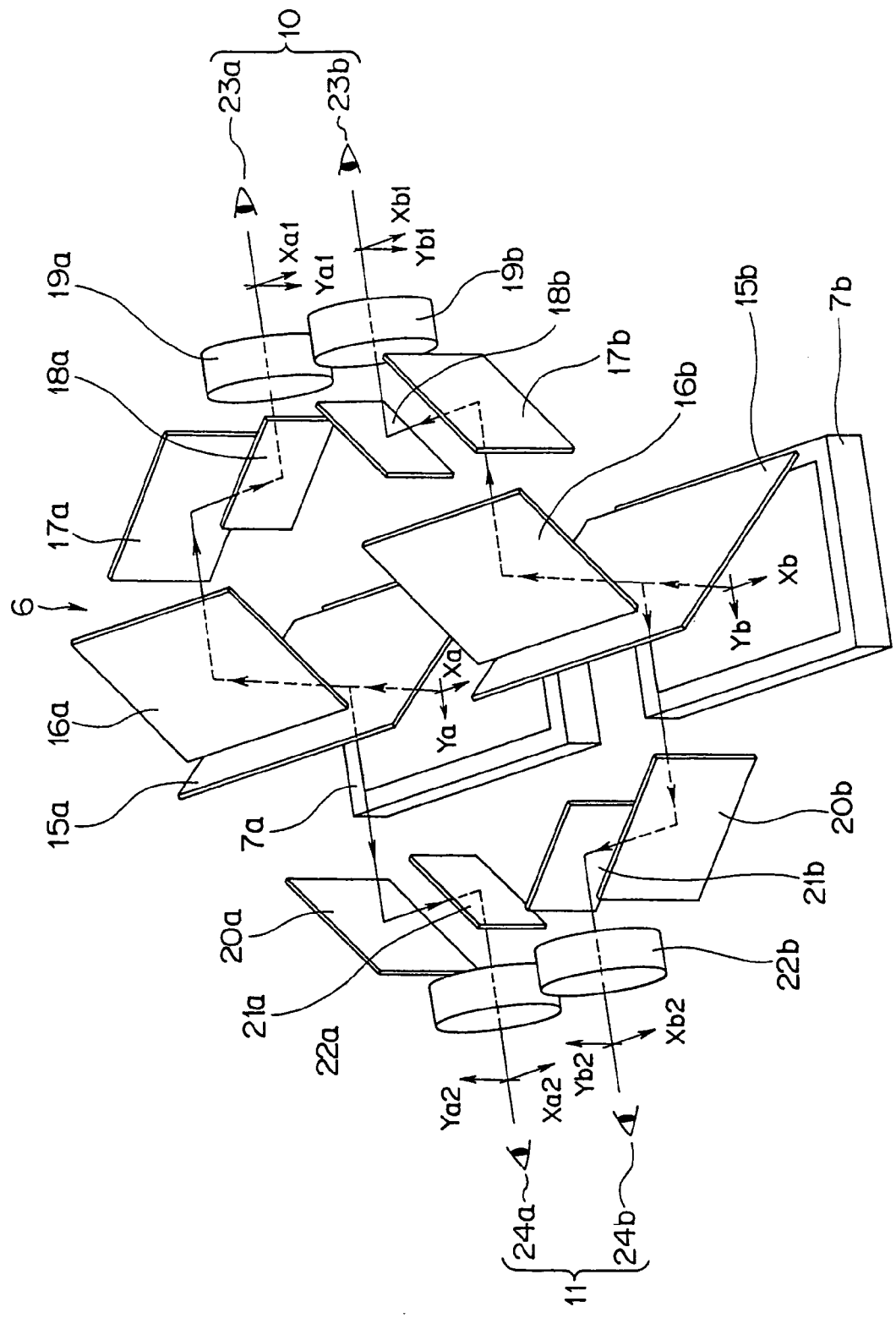
FIG. 3 is a block diagram which illustrates the construction and operation of the display unit in the three-dimensional observation system of the first embodiment.
Figure 4:
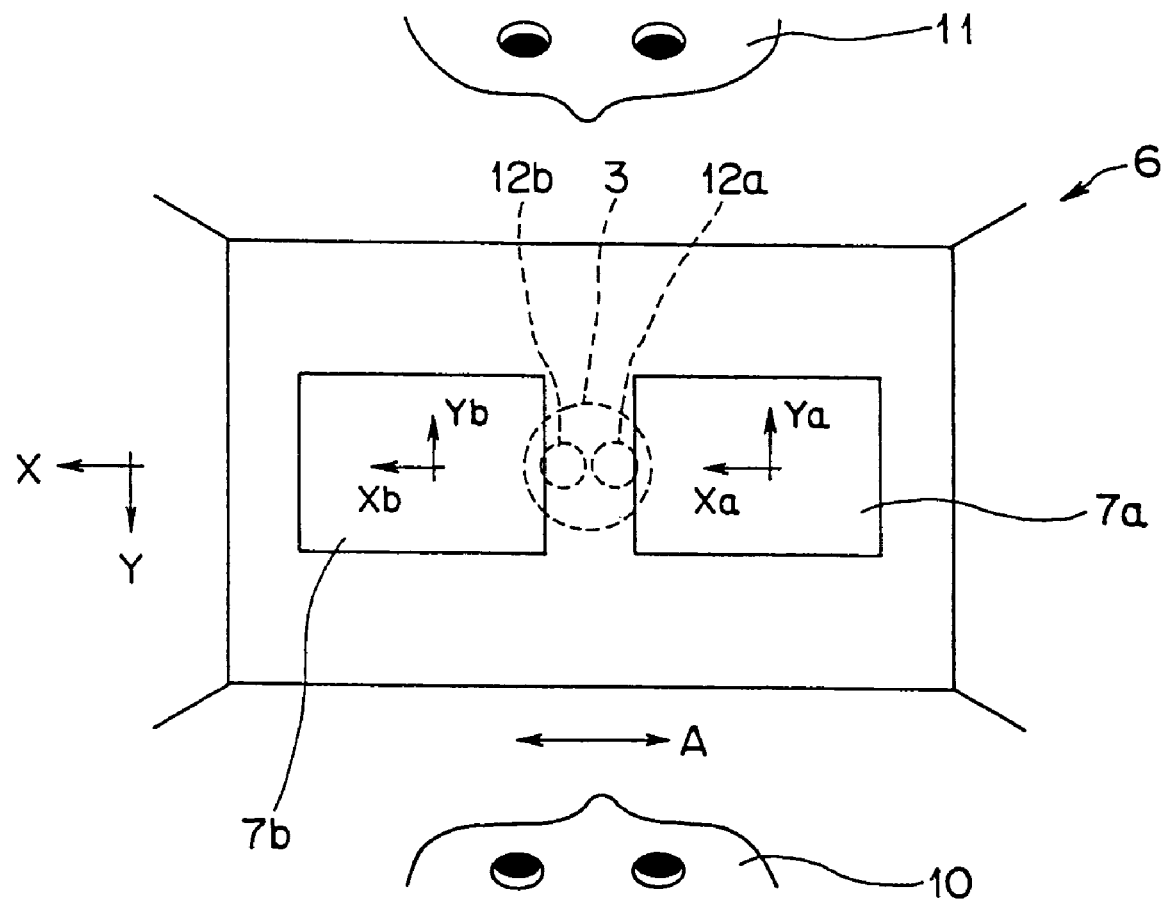
FIG. 4 is an explanatory diagram which illustrates the conditions of use of the three-dimensional observation system of the first embodiment.
Figure 5:
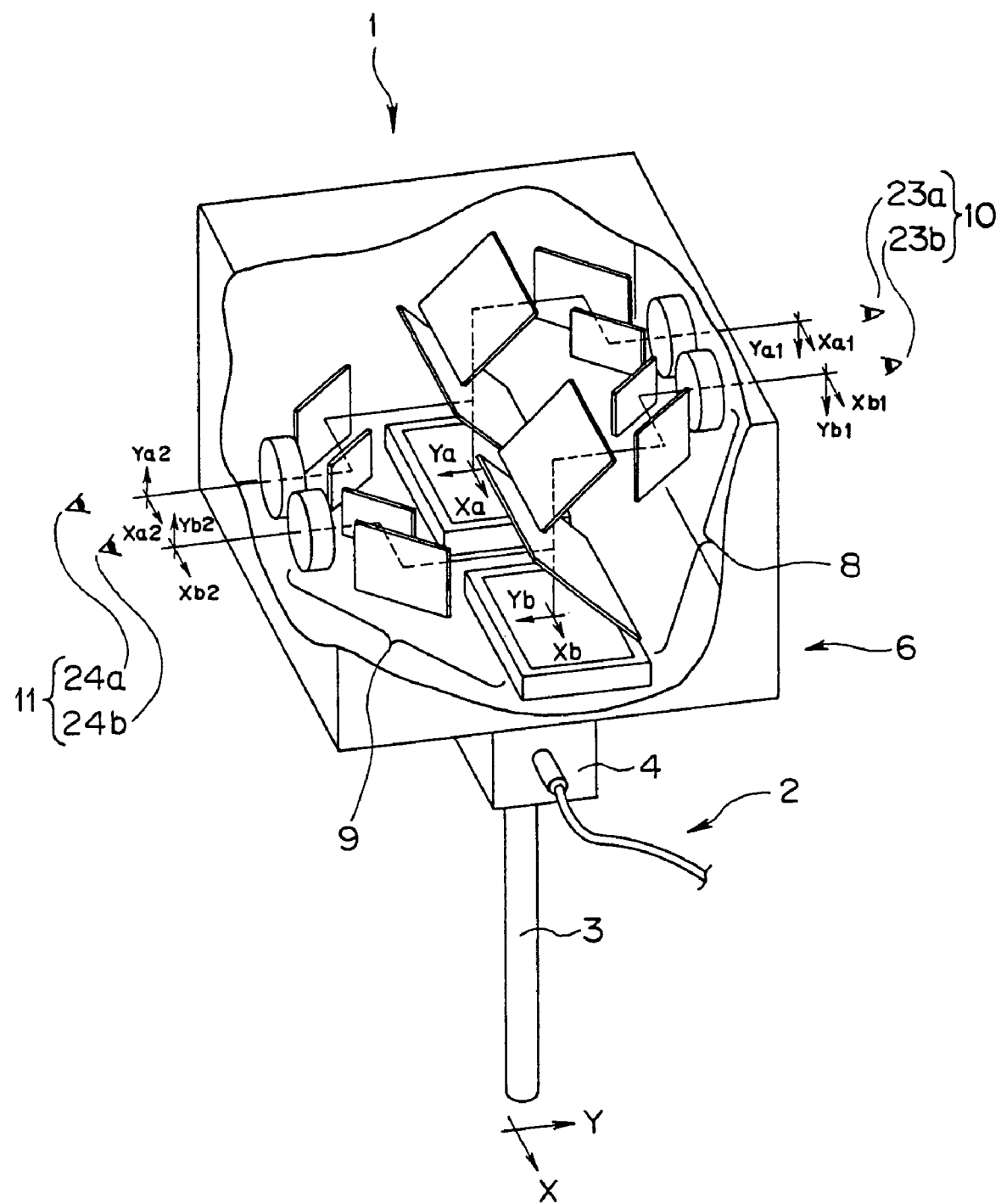
FIG. 5 is an explanatory diagram which illustrates the operation during use of the three-dimensional observation system of the first embodiment.
Figure 6A:
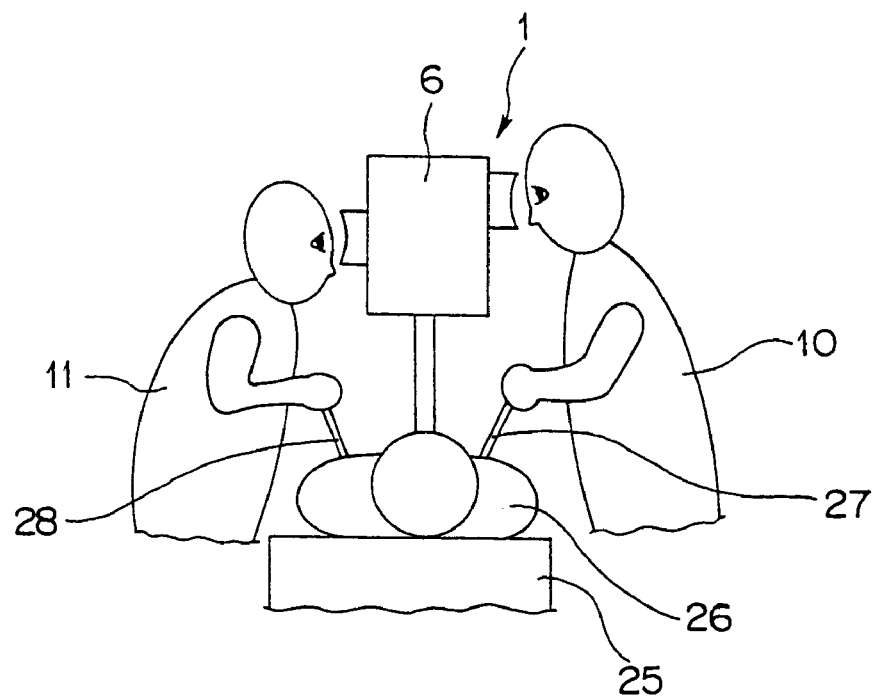
FIG. 6A is an explanatory diagram which illustrates the conditions of use by the operating surgeon and assistants in the three-dimensional observation system of the first embodiment.
Figure 6B:
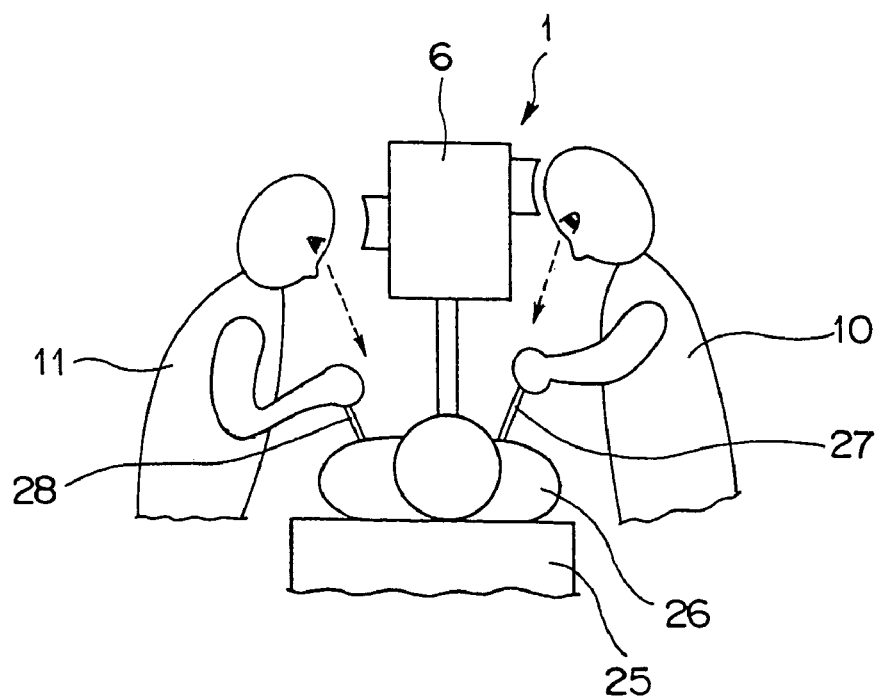
FIG. 6B is an explanatory diagram which illustrates the conditions of use by the operating surgeon and assistants in the three-dimensional observation system of the first embodiment.

FIG. 1 is a perspective view which shows the overall construction of a three-dimensional observation system constituting a first embodiment of the present invention, FIG. 2 is a block diagram which shows the schematic construction of the three-dimensional observation system of the first embodiment, FIG. 3 is a block diagram which illustrates the construction and operation of the display unit in the three-dimensional observation system of the first embodiment, FIG. 4 is an explanatory diagram which illustrates the conditions of use of the three-dimensional observation system of the first embodiment, FIG. 5 is an explanatory diagram which illustrates the operation during use of the three-dimensional observation system of the first embodiment, and FIGS. 6A and 6B are explanatory diagrams which illustrate the conditions of use by the operating surgeon and assistants in the three-dimensional observation system of the first embodiment.

As is shown in FIG. 1, the three-dimensional observation system constituting a first embodiment of the present invention comprises a three-dimensional endoscope 2 which is used to pick up the image of an observation site inside a body cavity of a patient constituting the object of observation during a surgical procedure, and a display unit 6 which is disposed on the proximal end portion of this three-dimensional endoscope 2, and which displays images of the observation site captured by the three-dimensional endoscope 2; this three-dimensional observation system 1 is used being attached to the operating table.

The three-dimensional endoscope 2 comprises an optical unit 3 which takes in two images of the observation site that have a mutual parallax, and an image pickup unit 4 which produces respective image-picked-up signals by subjecting the two images of the observation site taken in by the optical unit 3 to a photoelectric conversion.

The display unit 6 comprises a first liquid crystal display panel (hereafter referred to as "LCD=liquid crystal display) 7a and second LCD 7b which respectively display observation images based on the two image-picked-up signals produced by the image pickup unit 4 of the three-dimensional endoscope 2, and a first optical system 8 and second optical system 9 which guide the respective observation images displayed on the first LCD 7a and second LCD 7b to the respective eyes of an operating surgeon 10 constituting a first observer, and an assistant 11 constituting a second observer.

The construction of the three-dimensional endoscope 2 may be described in detail as follows with reference to FIG. 2: a first objective lens 12a and second objective lens 12b are disposed on the distal end of the optical unit 3, which is inserted into the body cavity, and which takes in images of the observation site; these two objective lenses 12a and 12b are disposed such that the lenses have a parallax with a specified interval. In other words, the first objective lens 12a and second objective lens 12b can take in images of the observation site that have a parallax respectively.

The images of the observation site taken in by these two objective lenses 12a and 12b are guided as light to the image pickup unit 4 by a relay optical system not shown in the figures.

In the image pickup unit 4, a first image pickup element 13a and second image pickup element 13b are respectively disposed in the image-focusing positions of the images of the observation site that are taken in and guided by the first objective lens 12a and second objective lens 12b of the optical unit 3. These two image pickup elements 13a and 13b are respectively connected to an image signal processing device 14 by an electrical cable 5.

The image pickup elements 13a and 13b produce captured image signals by subjecting the formed images of the observation site to a photoelectric conversion. For example, CMOS sensors, CCDs (charge coupled devices) or the like are used as these image pickup elements. These image pickup elements 13a and 13b subject the images of the observation site to a photoelectric conversion under the driving control of the image signal processing device 14 and output the captured image signals thus produced.

The image signal processing device 14 performs respective driving control of the image pickup elements 13a and 13b, and produces standard video signals by performing specified signal processing on the captured image signals from the respective image pickup elements 13a and 13b. These video signals are respectively supplied to the first LCD 7a and second LCD 7b of the display unit 6 via an electrical cable 5, so that observation images of the observation site are displayed.

Specifically, the image of the observation site taken in by the first objective lens 12a of the optical unit 3 is converted into an captured image signal by the first image pickup element 13a, and this captured image signal is displayed as an observation image on the first LCD 7a after being subjected to specified signal processing by the image signal processing device 14. Furthermore, the image of the observation site taken in by the second objective lens 12b of the optical unit 3 is converted into an captured image signal by the second image pickup element 13b, and this captured image signal is displayed as an observation image on the second LCD 7b after being subjected to specified signal processing by the image signal processing device 14.

Next, the construction of the display unit 6 will be described with reference to FIG. 3. A substantially cubical housing is disposed on the proximal end portion of the three-dimensional endoscope 2, and the first LCD 7a and second LCD 7b which display observation images on the basis of the video signals that are captured by the three-dimensional endoscope 2 and subjected to signal processing by the image signal processing device 14 are disposed on the bottom surface of this housing.

A first half-mirror 15a and second half-mirror 15b are respectively disposed on the upper sides (with respect to the figure) of the first LCD 7a and second LCD 7b at an angle of approximately 45 degrees. These half-mirrors 15a and 15b are arranged so as to split the light of the observation images respectively displayed on the LCDs 7a and 7b into the first optical system 8 and second optical system 9.

On the upper sides (with respect to the figure) of the first and second half-mirrors 15a and 15b, the following are disposed: first reflective mirrors 16a and 16b, second reflective mirrors 17a and 17b and third reflective mirrors 18a and 18b which respectively reflect the light that is transmitted through the half-mirrors 15a and 15b; and a first optical system 8 which respectively guides the light of the observation images from the first LCD 7a and second LCD 7b (that has thus been reflected respectively) to ocular lenses 19a and 19b used by the operating surgeon 10.

Furthermore, a second optical system is disposed, wherein the light of the observation images from the first LCD 7a and second LCD 7b that is reflected by the first and second half-mirrors 15a and 15b is respectively reflected by fourth reflective mirrors 20a and 20b and fifth reflective mirrors 21a and 21b, and is guided to ocular lenses 22a and 22b used by the assistant 11.

Specifically, the observation images displayed on the first LCD 7a and second LCD 7b can be enlarged and observed through the ocular lenses 19a and 19b used by the operating surgeon 10, and the same observation images displayed on the first LCD 7a and second LCD 7b can be enlarged and observed through the ocular lenses 22a and 22b used by the assistant 11. In other words, the operating surgeon 10 and assistant 11 can simultaneously observe a three-dimensional image of the observation site displayed on the first LCD 7a and second LCD 7b.

When the orientation of the observation images displayed on the first LCD 7a and second LCD 7b and the orientation of the images respectively observed by the operating surgeon 10 and assistant 11 are considered, the arrows indicated by Xa (or Xb) and Ya (or Yb) in the figure (in the observation images displayed on the first LCD 7a (or second LCD 7b)) are observed in the directions indicated by the arrows Xa1 (or Xb1) and Ya1 (or Yb1) shown in the figure when observed by the operating surgeon 10. Similarly, these arrows are observed in the directions indicated by the arrows Xa2 (or Xb2) and Ya2 (or Yb2) when observed by the assistant 11.

Next, the positional relationship of the observation images observed by the operating surgeon 10 and assistant 11 in this three-dimensional observation system will be described with reference to FIG. 4. The dotted lines in this FIG. 4 indicate the optical unit 3 of the three-dimensional endoscope 2, and the first objective lens 12a and second objective lens 12b disposed in this optical unit 3. The images of the observation site taken in by the first and second objective lenses 12a and 12b are subjected to specified signal processing in the image pickup unit 4 and image signal processing device 14, and respective observation images are displayed on the first LCD 7a and second LCD 7b disposed in the display unit 6 based on the video signals produced by this signal processing. With respect to this display unit 6, the operating surgeon 10 and assistant 11 respectively view three-dimensional images of the observation site via the ocular lenses 19a and 19b of the display unit 6 on the side of the operating surgeon 10 and the ocular lenses 22a and 22b on the side of the assistant 11 in positions facing each other.

During such observation of three-dimensional images, the parallax directions of the first and second objective lenses 12a and 12b, first and second LCDs 7a and 7b and operating surgeon 10 and assistant 11 are all unified in the direction indicated by the arrow A in FIG. 4. Furthermore, the directions indicated by the arrows X and Y on the site that is the object of observation are respectively shown as the arrows Xa and Ya on the display screen of the first LCD 7a, and as the arrows Xb and Yb on the display screen of the second LCD 7b. The observation images displayed on the first and second LCDs 7a and 7b are guided by the first optical system 8 and second optical system 9, and are respectively observed by the operating surgeon 10 and assistant 11.

The conditions under which the observation images displayed on the first and second LCDs 7a and 7b are guided to the eyes 23a and 23b of the operating surgeon 10 and the eyes 24a and 24b of the assistant 11 via the first optical system 8 and second optical system 9 will be described with reference to FIG. 5.

The directions of the arrows Xa1, Xb1, Ya1 and Yb1 shown in the same figure correspond to the directions of the arrows X and Y on the site that is the object of observation for the operating surgeon 10. Such a direction of observation of three-dimensional images coincides with the direction of observation in a case where the operating surgeon 10 directly observes the site that is the object of observation with his own eyes, without using the three-dimensional observation system 1. Similarly, the directions of the arrows Xa2, Xb2, Ya2 and Yb2 shown in the same figure correspond to the directions of the arrows X and Y on the site that is the object of observation for the assistant 11. This coincides with the direction of observation in a case where the assistant 11 directly observes the site that is the object of observation with his own eyes, without using the three-dimensional observation system 1.

Accordingly, although the directions of observation are different, the operating surgeon 10 and assistant 11 can observe the same three-dimensional image, and the three-dimensional image can be observed in a state in which both the operating surgeon 10 and the assistant 11 are facing forward.

As a result, when a surgical procedure is performed using this three-dimensional observation system 1 as shown in FIGS. 6A and 6B, the operating surgeon 10 and assistant 11 can both perform an endoscopic surgical procedure by operating respective surgical operating instruments 27 and 28 while observing a three-dimensional image of the interior of the body cavity of the patient 26 lying on the operating table 25 via the three-dimensional observation system 1.

In other words, when the operating surgeon 10 and assistant 11 operate the respective surgical operating instruments 27 and 28, the operating surgeon and assistant can perform procedures while observing a three-dimensional image by looking at the display unit 6 of the three-dimensional observation system 1 which is located in front of the operating surgeon and assistant as shown in FIG. 6A.

Furthermore, by turning their faces such that their line of sight is shifted from the display unit 6, the operating surgeon 10 and assistant 11 can view the area at hand directly, and observe and grasp their surrounding conditions as shown in FIG. 6B.

Since the three-dimensional observation system 1 of the first embodiment of the present invention comprises: a three-dimensional endoscope 2 which produces observation video signals by performing specified signal processing on image-picked-up signals after taking in the light from a site that is the object of observation by first and second objective lenses which are disposed such that these lenses have a specified parallax, and captured and produced by first and second image pickup elements 13a and 13b; and a display unit 6 which has first and second LCDs 7a and 7b disposed with a specified parallax that display observation images on the basis of the observation video images produced by this three-dimensional endoscope 2, and having first and second optical systems 8 and 9 that guide the observation images displayed on the first and second LCDs 7a and 7b such that the same state as that of direct viewing of the observation site by the operating surgeon 10 and assistant 11 is produced. Thus, observers such as the operating surgeon 10, assistant 11 and the like can observe three-dimensional images while facing each other. Accordingly, there is no need to perform surgical procedures in forced posture, so that fatigue of the observers is reduced; furthermore, since the operating surgeon 10 and assistant 11 can both view the same observation image in a direction that coincides with the directions of their own lines of sight, their mutual sense of direction is easily grasped, so that delicate surgical procedures can be performed in a short time.

Furthermore, the operating surgeon 10 and assistant 11 can grasp their surrounding conditions by turning their faces from the three-dimensional observation system 1, so that communication with other persons cooperating in the surgical procedure is facilitated.

Figure 7:
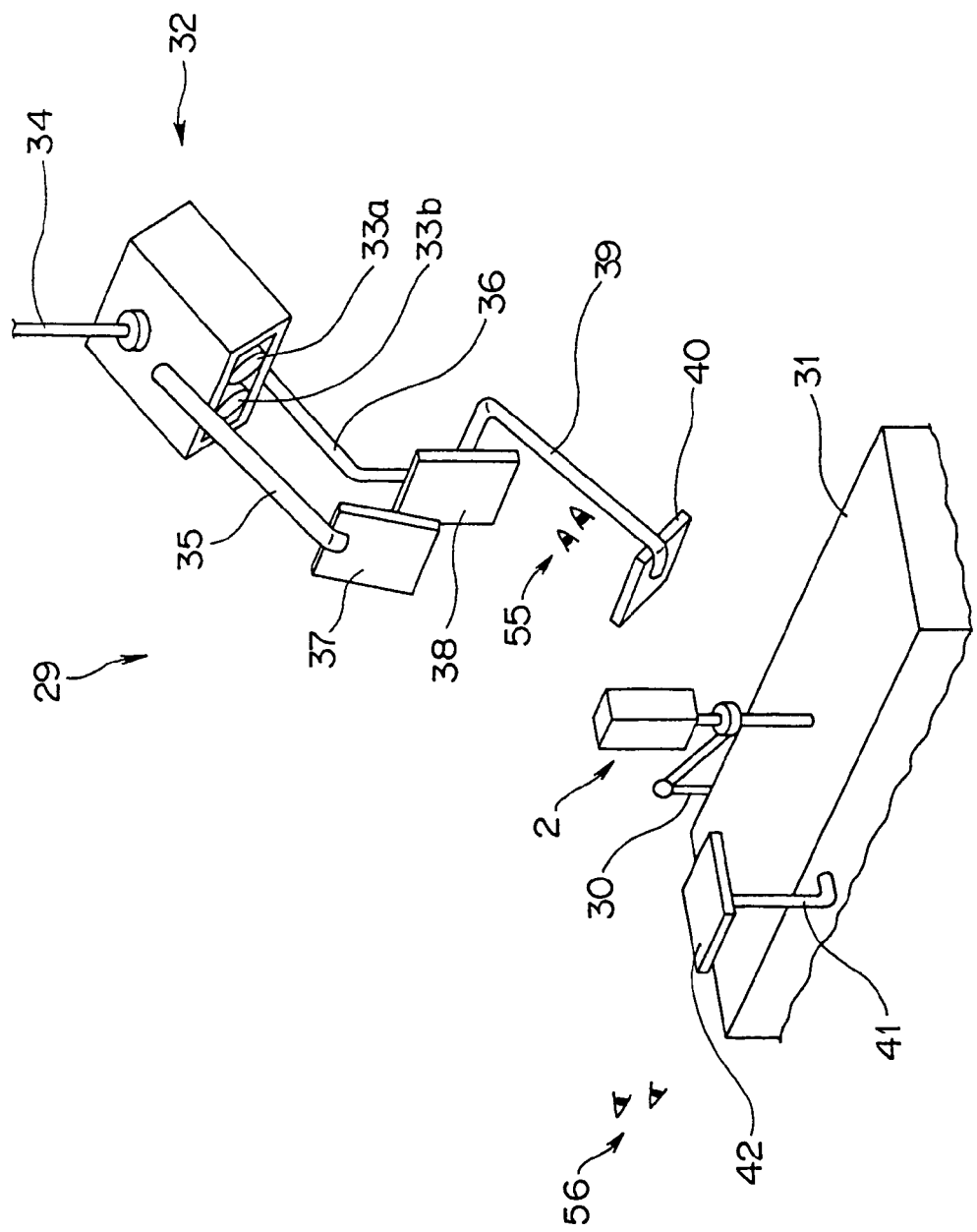
FIG. 7 is a perspective view which shows the overall construction of a three-dimensional observation system constituting a second embodiment of the present invention.
Figure 8:
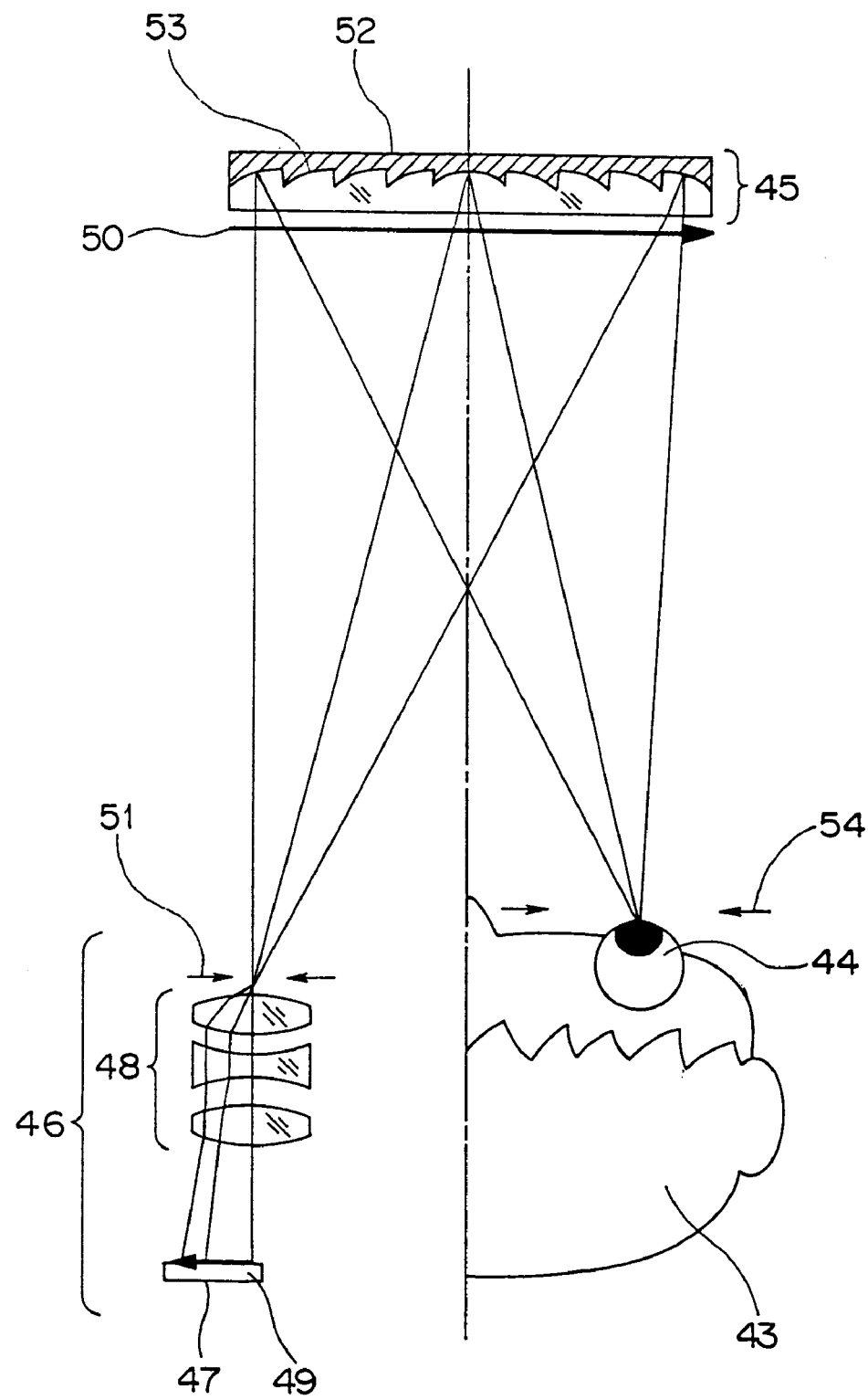
FIG. 8 is an explanatory diagram which illustrates the principle of observation of three-dimensional images in the three-dimensional observation system of the second embodiment.
Figure 9:
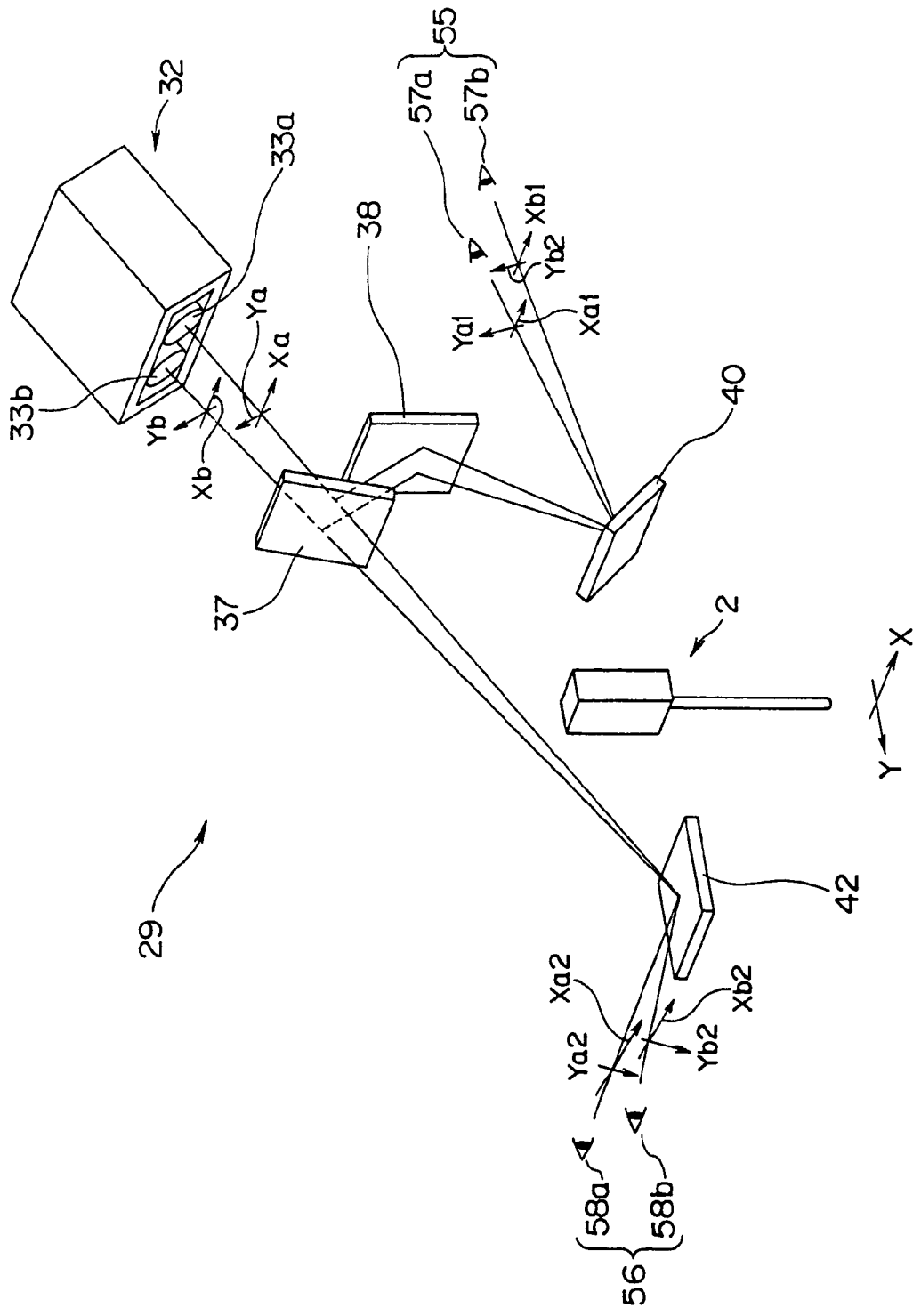
FIG. 9 is an explanatory diagram which illustrates the light guiding action of the light of observation images in the three-dimensional observation system of the second embodiment.
Figure 10:
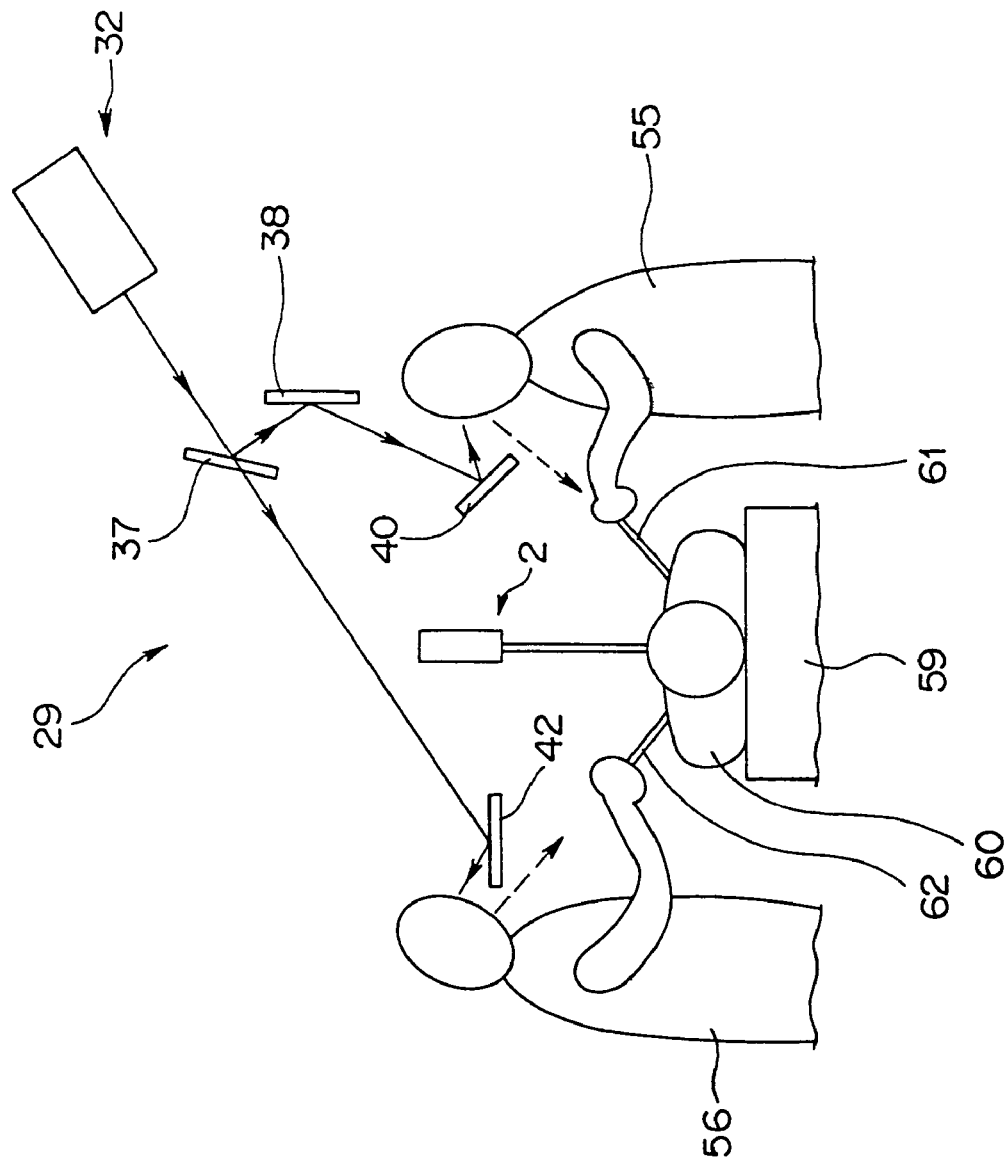
FIG. 10 is an explanatory diagram which illustrates the conditions of a surgical procedure using the three-dimensional observation system of the second embodiment.

Next, a second embodiment of the three-dimensional observation system of the present invention will be described with reference to FIGS. 7 through 10. FIG. 7 is a perspective view which shows the overall construction of a three-dimensional observation system constituting a second embodiment of the present invention, FIG. 8 is an explanatory diagram which illustrates the principle of observation of three-dimensional images in the three-dimensional observation system of the second embodiment, FIG. 9 is an explanatory diagram which illustrates the light guiding action of the light of observation images in the three-dimensional observation system of the second embodiment, and FIG. 10 is an explanatory diagram which illustrates the conditions of a surgical procedure using the second embodiment of the three-dimensional observation system of the present invention.

As is shown in FIG. 7, the three-dimensional observation system 29 of the second embodiment of the present invention is devised such that a scope holder 30 is attached to the operating table 31, and the three-dimensional endoscope 2 same as in the first embodiment held by this scope holder 30.

An image projection unit 32 comprising first image projection means 33a and second image projection means 33b is disposed above the vicinity of the operating table 31. The system is devised such that observation images are displayed and projected from the first and second image projection means 33a and 33b of this image projection unit 32 on the basis of video signals that, after picking up the image by the three-dimensional endoscope 2, are subjected to specified signal processing by an image signal processing device not shown in the figures. Furthermore, this image projection unit 32 is held by being attached to a stand (not shown in the figures) by a holding member 34.

A first mirror holding arm 35 and a second mirror holding arm 36 are respectively attached such that these arms extend from the upper and lower surfaces of the housing of the image projection unit 32; a half-mirror 37 is attached and fastened to the distal end of the first mirror holding arm 35, and a reflective mirror 38 is attached and fastened to the distal end of the second mirror holding arm 36.

Furthermore, a panel holding arm 39 is attached to the reflective mirror 38, and a first Fresnel concave mirror panel 40 is attached and fastened to the distal end of this panel holding arm 39.

Furthermore, a second Fresnel concave mirror panel 42 is attached and fastened to the operating table 31 by a panel holding arm 42, one end of which is fastened to the operating table 31.

The light of observation images that are respectively projected from the first and second image projection means 33a and 33b of the image projection unit 32 is splitted into two by the half-mirror 37. The projected observation images that are reflected by this half-mirror 37 are reflected by the reflective mirror 38 and projected onto the first Fresnel concave mirror panel 40, and the projected observation images that pass through the half-mirror 37 are projected onto the second Fresnel concave mirror panel 42.

In cases where a surgical procedure is performed using the three-dimensional observation system 29 constructed as described above, the operating surgeon 55 stands in front of the first Fresnel concave mirror panel 40, and performs the surgical procedure while observing a three-dimensional image that is displayed on the first Fresnel concave mirror panel 40. Furthermore, the assistant 56 stands in front of the second Fresnel concave mirror panel 42, and assists in the surgical procedure while observing a three-dimensional image that is displayed on the second Fresnel concave mirror panel 42.

The principle of three-dimensional image observation based on the first and second Fresnel concave mirror panels 40 and 42 of the three-dimensional observation system 29 of this second embodiment will be described with reference to FIG. 8.

The symbol 43 in FIG. 8 indicates an observer, which may be either the operating surgeon 55 or the assistant 56, and the symbol 44 indicates the left eye of this observer 43.

Furthermore, the symbol 45 in the figure indicates the cross section of the Fresnel concave mirror panel used in the first or second Fresnel concave mirror panel 40 or 42, and the symbol 46 indicates the left eye projection means corresponding to the second image projection means 33b of the image projection unit 32, which corresponds to the left eye 44 of the observer 43.

These left eye projection means 46 comprises an LCD 47 on which the left eye observation image captured by the three-dimensional endoscope 2 is displayed, a projection optical system 48 comprising a plurality of projection lenses that project the image 49 displayed on this LCD 47, and an emission pupil which adjusts the quantity of light of the projected image that is projected from this projection optical system 48.

The image 49 that is projected from these left eye projection means 46 is enlarged, projected and displayed as a projected image 50 on the Fresnel concave mirror panel 45. In this Fresnel concave mirror panel 45, a Fresnel concave mirror 53 with a positive power is disposed on the surface on which the image 49 projected from the left eye projection means 46 is enlarged and projected, and a mirror coating 52 is formed on the back surface of this Fresnel concave mirror 53. The projected image 50 that is enlarged and projected on this Fresnel concave mirror panel 45 enters the left eye 44 of the observer 43 via an emission pupil 54 which adjusts the quantity of light of the projected image, and which is disposed in front of this left eye 44 of the observer 43. Furthermore, a right eye observation image is also similarly emitted in the case of the right eye, so that the images can be observed as a three-dimensional image.

In other words, the image 49 displayed on the LCD 47 is projected as a projected image 50 on the Fresnel concave mirror panel 45 by the image projection optical system 48. The projected image 50 is projected into the left eye 44 of the observer 43 by the lens action of the Fresnel concave mirror 53 that constitutes this Fresnel concave mirror panel 45. In this case, projection is performed such that the emission pupil 51 of the left eye projection means 46 is superimposed on the left eye 44 of the observer 43. In other words, the light received from the image projection means 46 is reflected, and is focused only in the vicinity of the left eye 44 of the observer 43. Accordingly, the observer 43 can observe the projected image from the left eye image projection means 46 with the left eye 44.

Furthermore, although this is not shown in the figures, the projected image from the right eye projection means is also similarly projected into the right eye of the observer. Accordingly, three-dimensional observation is possible by respectively observing different images that have a parallax with the left and right eyes.

Specifically, as is shown in FIG. 9, two images with a parallax that are captured by the three-dimensional endoscope 2 are respectively projected by the first and second image projection means 33a and 33b disposed in the image projection unit 32, and the light of the images that are projected from these first and second image projection means 33a and 33b is splitted into two by the half-mirror 37. The images reflected by this half mirror 37 are guided to the first Fresnel concave mirror panel 40 by the reflective mirror 38, and are reflected by this first Fresnel concave mirror panel 40 so that these images are guided to the eyes 57a and 57b of the operating surgeon 55 constituting the first observer.

The images that pass through the half-mirror 37 are projected onto the second Fresnel concave mirror panel 42, and are reflected by this second Fresnel concave mirror panel 42 so that these images are guided to the eyes 58a and 58b of the assistant 56 constituting the second observer.

As a result, the operating surgeon 55 and assistant 56 can observe three-dimensional images that are respectively displayed on the first and second Fresnel concave mirror panels 40 and 42, and the directions of the parallaxes of the three-dimensional endoscope 2, first and second image projection means 33a and 33b, operating surgeon 55 and assistant 56 are unified in the direction indicated by the arrow X in FIG. 9. Furthermore, the directions indicated by the arrows X and Y on the object of observation at the observation site of which image is picked up by the three-dimensional endoscope 2 are respectively projected as the arrows Xa, Ya, Xb and Yb (shown in the figure) from the first and second image projection means 33a and 33b, and are observed as the arrows Xa1 and Ya1 in the right eye 57a of the operating surgeon 55, and as the arrows Xb1 and Yb1 in the left eye 57 of the operating surgeon 55. This means that the operating surgeon 55 can observe a three-dimensional image with the same orientation as when the arrows X and Y on the object of observation are viewed directly. Furthermore, these directions are observed as the arrows Xb2 and Yb2 in the right eye 58b of the assistant 56, and as the arrows Xa2 and Ya2 in the left eye 58a of the assistant 56. Accordingly, here as well, the assistant can observe a three-dimensional image with the same orientation as when the arrows X and Y on the object of observation are viewed directly.

As is shown in FIG. 10, a surgical procedure using the three-dimensional observation system 29 of the second embodiment constructed as described above is performed as follows: specifically, the image of the interior of the body cavity of the patient 60 lying on the operating table 59 is picked up by the three-dimensional endoscope 2, and the observation images thus captured are projected from the image projection unit 32 onto the first and second Fresnel concave mirror panels 40 and 42 which are respectively disposed in front of the operating surgeon 55 and assistant 56 who face each other with the operating table 59 interposed.

While respectively facing straight forward, the operating surgeon 55 and assistant 56 can perform a surgical procedure using surgical operating instruments 61 and 62 on the basis of observation images projected and displayed on the first and second Fresnel concave mirror panels 40 and 42.

As a result, the operating surgeon 55 and assistant 56 can observe a three-dimensional image of the observation site seen from the same direction as when the observation site of the patient is viewed by the operating surgeon and assistant from their own locations, and can view the area at hand and the surrounding conditions by shifting the orientation of their faces from the Fresnel concave mirror panels 40 and 42 that they are viewing.

Accordingly, since the operating surgeon 55 and assistant 56 can perform a surgical procedure while observing a three-dimensional image in a comfortable posture facing straight forward with respect to the operating table 59, fatigue during the surgical procedure can be alleviated. Furthermore, since the operating surgeon 55 and assistant 56 can simultaneously observe the same observation image, and since the direction of the three-dimensional image and the direction of direct vision of the observers are the same, delicate surgical procedures can be efficiently performed without any confusion in the operation of the surgical operating instruments.

Furthermore, the observers (such as the operating surgeon 55, assistant 56 and the like) can grasp the surrounding conditions by shifting the orientation of their faces from the first and second Fresnel concave mirror panels 40 and 42, so that communication with other persons cooperating in the surgical procedure is facilitated.

Figure 11:
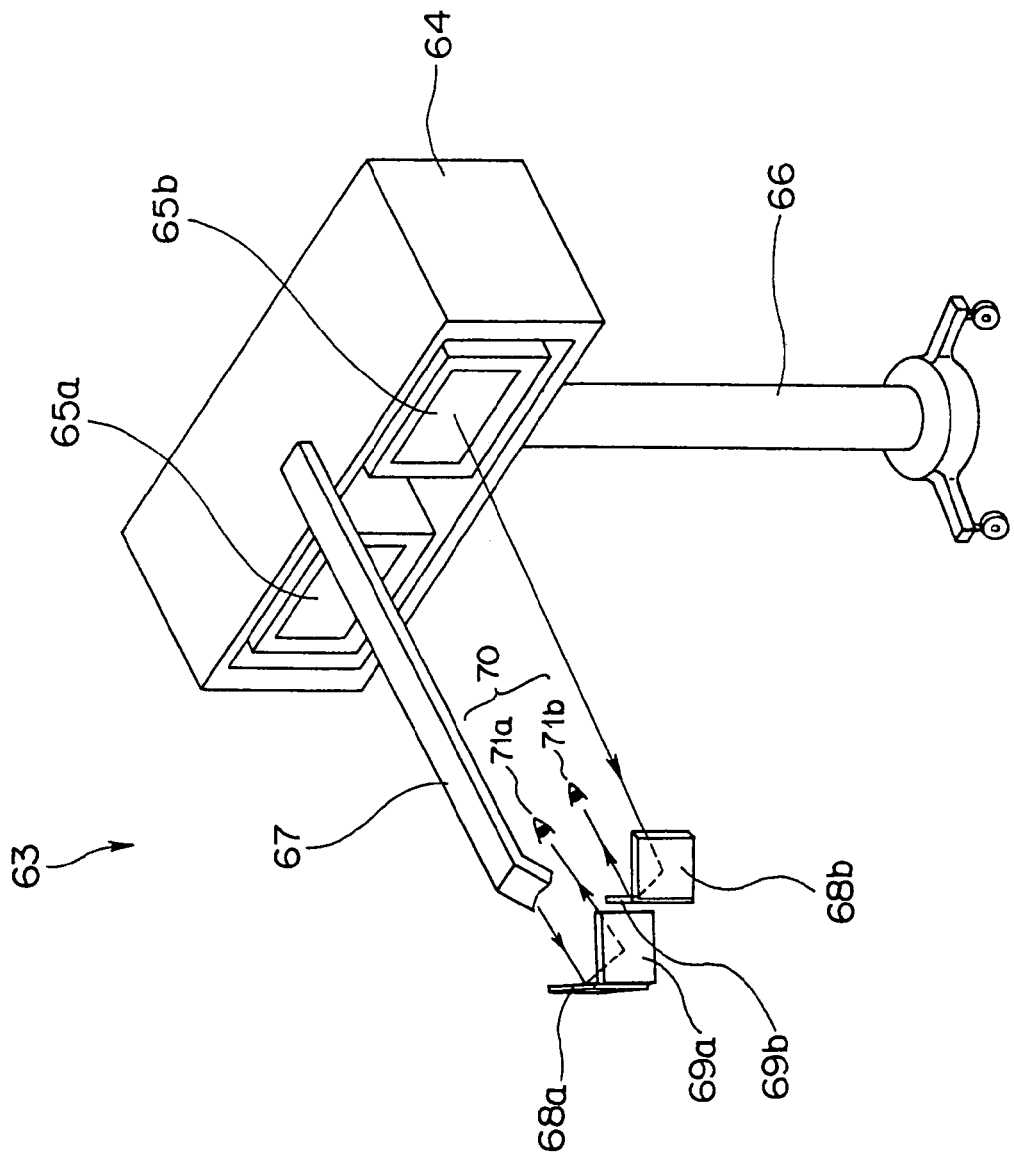
FIG. 11 is a perspective view which shows the overall construction of a three-dimensional observation system constituting a third embodiment of the present invention.
Figure 12:
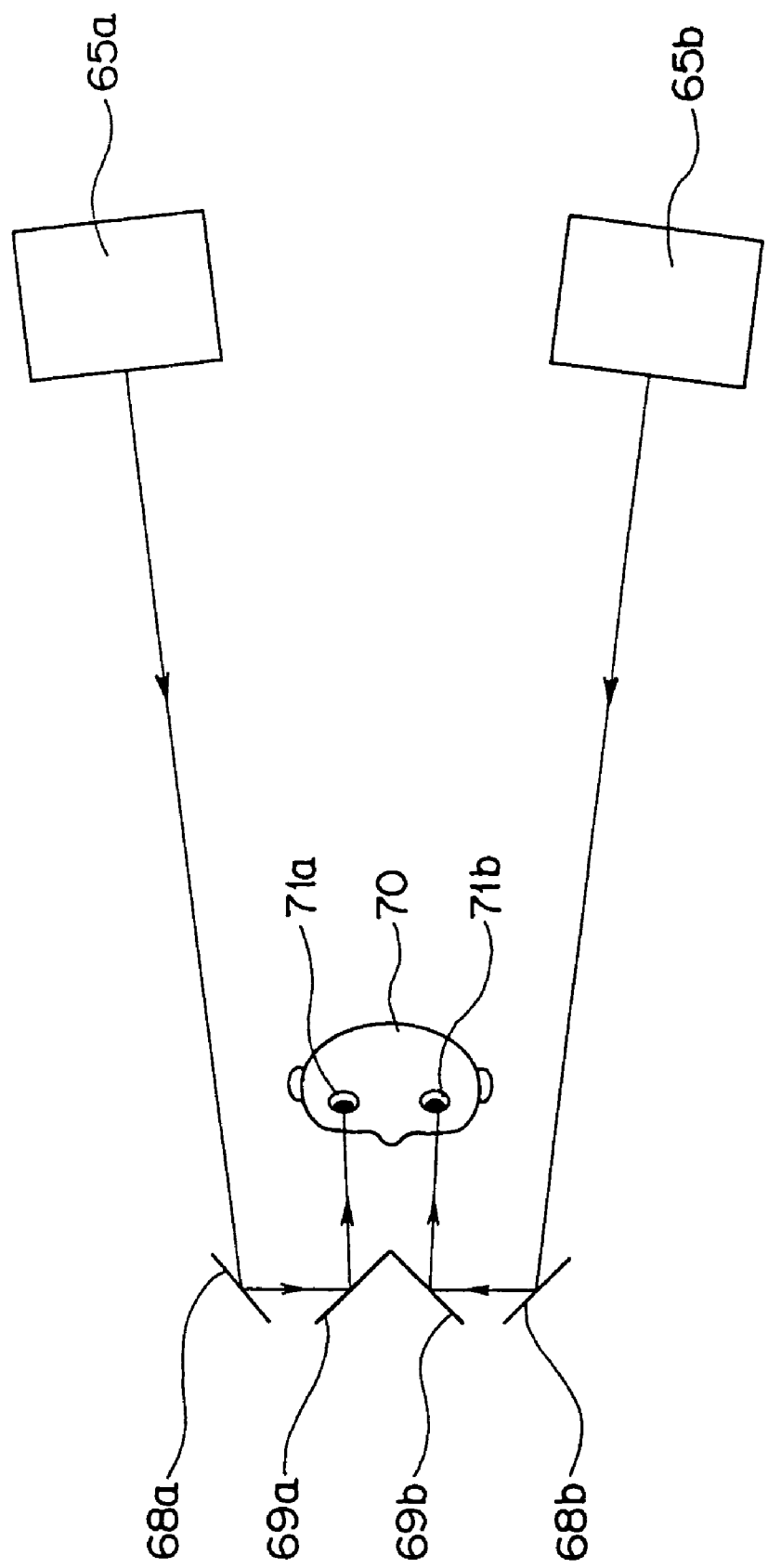
FIG. 12 is a plan view which illustrates the principle of operation of the three-dimensional observation system of the third embodiment.
Figure 13:
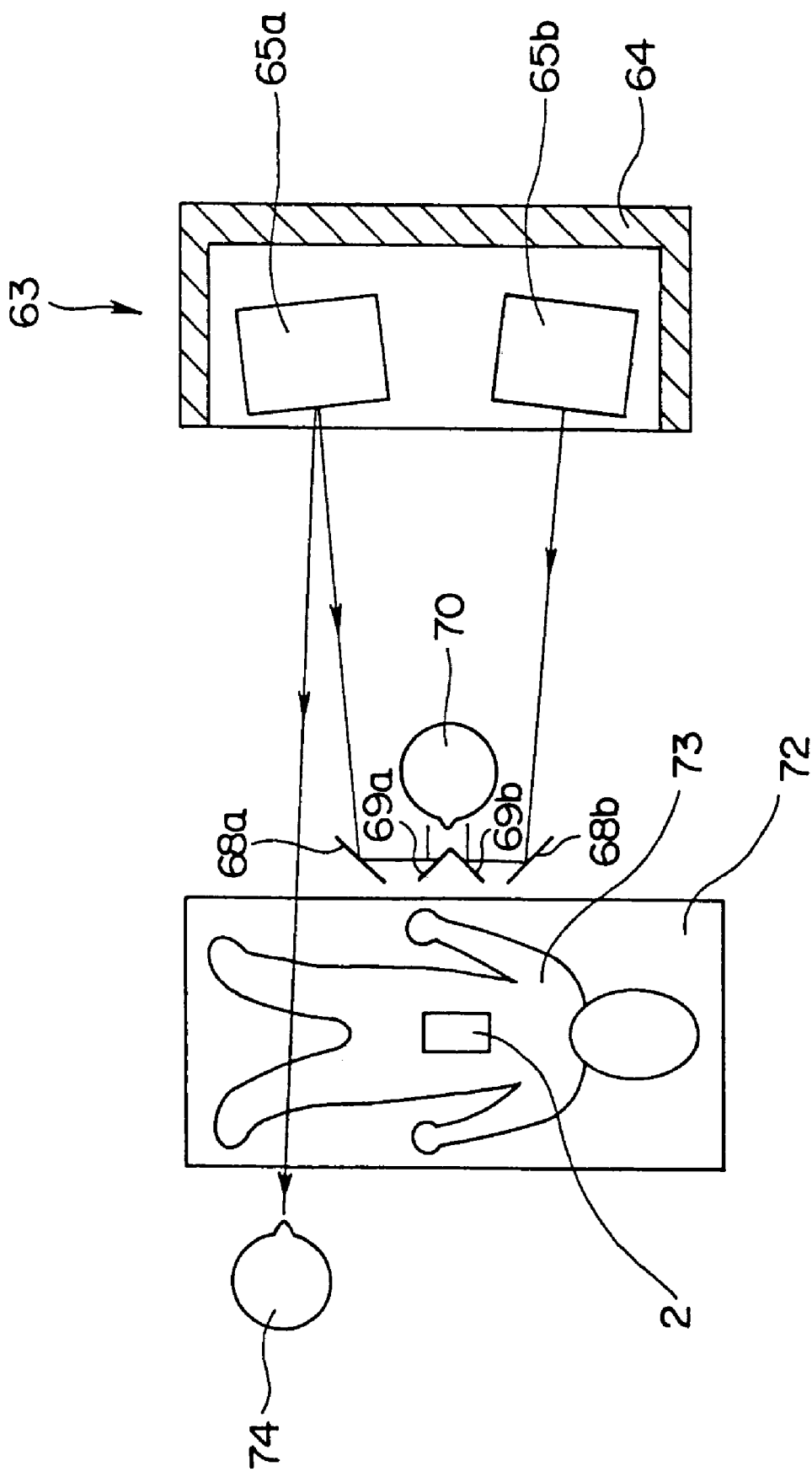
FIG. 13 is a plan view which illustrates the conditions of three-dimensional observation by the operating surgeon and assistants during a surgical procedure using the three-dimensional observation system of the third embodiment.
Figure 14:
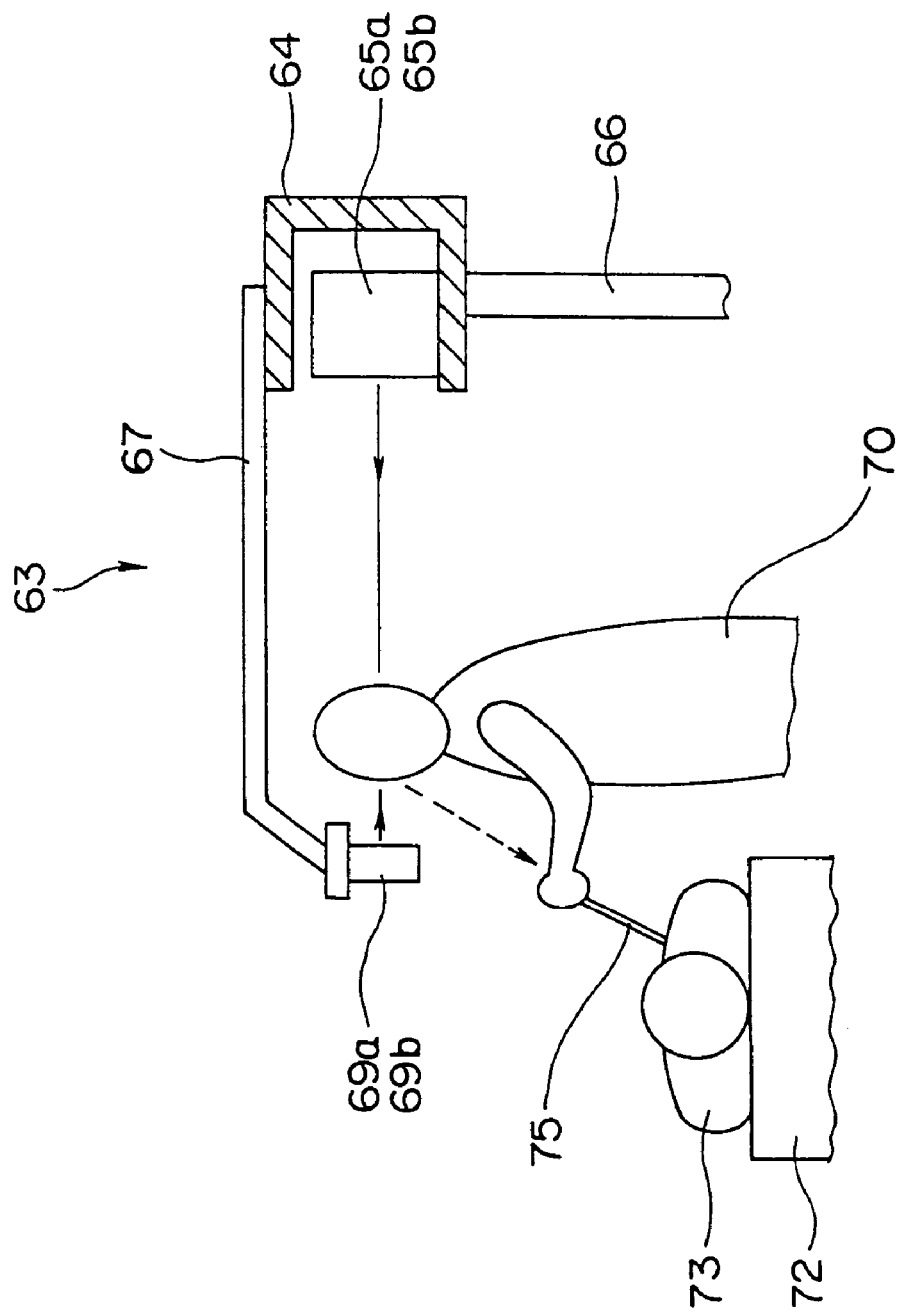
FIG. 14 is an explanatory diagram which illustrates the operation in a surgical procedure using the three-dimensional observation system of the third embodiment.

Next, a third embodiment of the three-dimensional observation system of the present invention will be described with reference to FIGS. 11 through 14. FIG. 11 is a perspective view which shows the overall construction of a three-dimensional observation system constituting a third embodiment of the present invention, FIG. 12 is a plan view which illustrates the principle of operation of the three-dimensional observation system of the third embodiment, FIG. 13 is a plan view which illustrates the conditions of three-dimensional observation by the operating surgeon and assistants during a surgical procedure using the three-dimensional observation system of the third embodiment, and FIG. 14 is an explanatory diagram which illustrates the operation in a surgical procedure using the third embodiment of the three-dimensional observation system of the present invention.

In the three-dimensional observation system of the third embodiment of the present invention, the display unit 64 that displays observation images on the basis of video signals produced as a result of picking-up of image performed by the three-dimensional endoscope 2 and specified signal processing performed by the image signal processing device 14 differs from the display units of the first and second embodiments.

In the display unit 64 of this third embodiment, a first monitor 65a and a second monitor 65b are provided to display observation images in accordance with two video signals having a mutual parallax that are produced by picking-up of image performed by the three-dimensional endoscope 2 and signal processing performed by the image signal processing device 14.

A stand 66 is provided for the display unit 64, in which the first and second monitors 65a and 65b are contained inside a housing, and the system is devised so that the first and second monitors 65a and 65b are disposed in a position located at the height of the eyes of the operating surgeon 70 by means of this stand 66.

A mirror holding arm 67 is attached so that this arm extends from the upper surface of the housing of the display unit 64. First mirrors 68a and 68b which are disposed at an angle of approximately 45 degrees with respect to the respective display screens of the first monitor 65a and second monitor 65b, and second mirrors 69a and 69b which are disposed at an angle of approximately 90 degrees with respect to the respective first mirrors 68a and 68b, are respectively disposed on the distal end portion of this mirror holding arm 67.

Specifically, the system is devised such that the observation image displayed on the first monitor 65a is reflected by the first mirror 68a and second mirror 69a, and is observed by the right eye 71a of the operating surgeon 70, and such that the observation image displayed on the second monitor 65b is reflected by the first mirror 68b and second mirror 69b, and is observed by the left eye 71b of the operating surgeon 71.

The principle of observation of three-dimensional images in the three-dimensional observation system 63 constructed as described above will be described with reference to FIG. 12.

A right eye observation image produced by performing signal processing on the picked-up image signal by the three-dimensional endoscope 2 and image signal processing device 14 is displayed on the first monitor 65a, and a left eye observation signal that is similarly produced is displayed on the second monitor 65b.

The observation images displayed on the first and second monitors 65a and 65b are respectively reflected by the first mirrors 68a and 68b disposed obliquely in front of the operating surgeon 70. The respective observation images reflected by the first mirrors 68a and 68b are further reflected by the second mirrors 69a and 69b disposed in front of the operating surgeon 70, and are guided to the left and right eyes 71a and 71b of the operating surgeon 70.

Specifically, the operating surgeon 70 can observe a three-dimensional image by viewing the image of the first monitor 65a with the right eye 71a and viewing the image of the second monitor 65b with the left eye 71b.

The conditions under which a surgical procedure is performed using the three-dimensional observation system 63 constructed as described above will be described with reference to FIGS. 13 and 14. For the patient 73 lying on the operating table 72, an image of an observation site inside a body cavity is picked up by the three-dimensional endoscope 2, which is attached and fastened to the operating table 72.

The operating surgeon 70 stands facing the patient 73 laying on this operating table 72; furthermore, the display unit 64 is disposed such that the second mirrors 69a and 69b are disposed directly in front of the operating surgeon 70.

Specifically, the three-dimensional endoscope 2 and the observation images displayed on the first and second monitors 65a and 65b on the basis of video signals produced by picking-up of image performed by this three-dimensional endoscope 2 and specified signal processing are caused to coincide with the direction of the parallax of the operating surgeon 70, so that the operating surgeon 70 can observe a three-dimensional image in a state in which this image is seen from the same direction as when the operating surgeon 70 observes the observation site directly with his own eyes.

Furthermore, other cooperating persons such as an assistant 74 or the like that assists the operating surgeon 70 can observe the same image as the operating surgeon 70 by directly viewing the observation images displayed on the first or second monitor 65a or 65b.

Moreover, as is shown in FIG. 14, when the operating surgeon 70 performs a surgical procedure by operating a surgical operating instrument 75 held in the hands while observing a three-dimensional image by means of the display unit 64, observation of the observation images can be accomplished merely by looking at the second mirrors 69a and 69b disposed directly in front, and the operating surgeon 70 can observe the area at hand and the surrounding conditions by shifting his line of sight from the second mirrors 69*a* and 69*b*.

In the third embodiment of the three-dimensional observation system of the present invention, as is described above, the operating surgeon 70 can observe a three-dimensional image of the observation site in the same orientation as the observation site actually faced by the operating surgeon 70, in a state in which the operating surgeon 70 faces the patient undergoing the surgical procedure; furthermore, other persons cooperating in the surgical procedure (who are assisting in the surgical procedure) can also simultaneously observe observation images in the same direction as when these cooperating persons are actually looking at the observation site themselves.

Furthermore, when the operating surgeon and assistant perform a surgical procedure while observing three-dimensional observation images, the operating surgeon and assistant can easily grasp surrounding conditions merely by shifting their line of sight to the area at hand or to their surroundings.

Accordingly, since persons cooperating in the surgical procedure, from the operating surgeon down, can observe three-dimensional images of the observation site and perform the surgical procedure in the most natural posture, i.e., facing the patient, delicate surgical procedures can be performed, and an alleviation of fatigue suffered by the operating surgeon and cooperating persons can be achieved, so that the efficiency of surgical procedures can be improved, and the operating time can be shortened.

The three-dimensional observation system of the present invention possesses the following merits: namely, observers such as the operating surgeon 10 (constituting a first observer), assistant 11 (constituting a second observer) and the like can observe three-dimensional images in a state in which these observers and the object of observation face each other, so that there is no need to perform surgical procedures in a forced posture. As a result, fatigue suffered by the observers is alleviated; furthermore, since the observers can both observe observation images in a direction that coincides with the direction of their own line of sight, delicate surgical procedures can be performed in a short time with the mutual sense of direction easily grasped. In addition, the observers can ascertain surrounding conditions merely by changing their line of sight, and communication with other persons cooperating in the surgical procedure is facilitated, so that the efficiency of such surgical procedures is improved.

Furthermore, embodiments or the like constructed by the partial combination or the like of the respective embodiments or the like are also included in the present invention.

In this invention, it is apparent that working modes different in a wide range can be formed on the basis of this invention without departing from the spirit and scope of the invention. This invention is not restricted by any specific embodiment except being limited by the appended claims.

What is claimed is:

1. A three-dimensional observation system comprising:
    image pickup means for picking up two images of an object of observation which have a parallax with respect to the object of observation;
    image display means for displaying the two images of the object of observation captured by the image pickup means so as to be observed as a three-dimensional image by an observer;
    light splitting means for splitting light representing the three-dimensional image emitted from the image display means; and
    optical means for guiding one of the lights representing the three-dimensional image split by the light spitting means to a position in front of the left and right eyes of a first observer who is squarely facing the object of observation, so that the parallax direction of the two images of the object of observation and the parallax direction of the first observer squarely facing the object of observation coincide, and guiding the other of the lights representing the three-dimensional image split by the light splitting means to a position in front of the left and right eyes of a second observer positioned squarely facing the object of observation from a direction different than the first observer, so that the parallax direction of the two images of the object of observation and the parallax direction of the second observer coincide.

2. A three-dimensional observation system according to claim 1, wherein the optical means comprises
    first optical means for guiding the two images displayed by the image display means respectively to the left and right eyes of a first observer from the front of the first observer, and
    second optical means for guiding at least one of the two images displayed by the image display means to the eyes of a second observer.

3. The three-dimensional observation system according to claim 2, wherein the first optical means causes the parallax direction of the two images of the object of observation and the parallax direction of the left and right eyes of the first observer to substantially coincide.

4. The three-dimensional observation system according to claim 3, wherein the second optical means guide the two images of the object of observation displayed by the image display means respectively to the left and right eyes of the second observer.

5. The three-dimensional observation system according to claim 4, wherein the second optical means causes the parallax direction of the two images of the object of observation and the parallax direction of the left and right eyes of the second observer to substantially coincide.

6. The three-dimensional observation system according to claim 1, wherein the optical means comprises
    first optical means for guiding the two images displayed by the image display means respectively to the left and right eyes of the first observer from the front of the first observer, and
    second optical means for guiding the two images displayed by the image display means respectively to the left and right eyes of the second observer from the front of the second observer.

7. The three-dimensional observation system according to claim 6, wherein the first optical means causes the parallax direction of the two images of the object of observation and the parallax direction of the left and right eyes of the first observer to substantially coincide, and the second optical means causes the parallax direction of the two images of the object of observation and the parallax direction of the left and right eyes of the second observer to substantially coincide.

8. The three-dimensional observation system according to claim 6, wherein the optical means is disposed so as to allow the first observer and the second observer to observe the same three-dimensional image when the first observer and the second observer both squarely face the object of observation from mutually different directions.

9. The three-dimensional observation system according to claim 1, wherein the optical means comprises:
    a plurality of reflecting means for reflecting the images from the light splitting means; and image observation means for visually observing the reflected images reflected by the reflecting means.

10. The three-dimensional observation system according to claim 9, wherein the image observation means is constituted by an ocular part having an ocular lens.

11. The three-dimensional observation system according to claim 1, wherein the image pickup means comprises
an optical unit for acquiring two images of the observation site having a parallax to each other, and
an image pickup unit for producing respective image-picked-up signals by photoelectrically converting the two images of the object of observation acquired by the optical unit.

12. The three-dimensional observation system according to claim 1, wherein the image pickup means and the image display means are disposed so as to be separated from each other.

13. The three-dimensional observation system according to claim 1, wherein the image display means one of the two images of the object of observation captured by the image pickup means on a first displaying means and the other of the two images of the object of observation on a second displaying means, for displaying the three-dimensional image based on the two images of the object of observation.

14. The three-dimensional observation system according to claim 1, wherein the light splitting means splits light of the images of the object of observation into two, and the optical means guides one of the lights of the images of the object of observation split by the light splitting means to a position in front of the left and right eyes of a first observer who is squarely facing the object of observation, so that the parallax direction of the image pickup means and the parallax direction of the first observer coincide, and guides the other of the lights of the images of the object of observation split by the light splitting means to a position in front of the left and right eyes of a second observer who is different from the first observer, so that the parallax direction of the image pickup means and the parallax direction of the second observer coincide, thus causing a three-dimensional image to be displayed.

15. The three-dimensional observation system according to claim 1, wherein the light splitting means is a half mirror for transmitting one of the lights representing the three-dimensional image and reflecting the other of the lights representing the three-dimensional image.

16. A three-dimensional observation system comprising:
image pickup means for picking up two images of an object of observation which have a parallax with respect to the object of observation;
image display means for displaying the two images of the object of observation captured by the image pickup means so as to be observed as a three-dimensional image by an observer;
light splitting means for splitting light representing the three-dimensional image emitted from the image display means;
a Fresnel concave mirror panel; and
optical means for guiding one of the lights representing the three-dimensional image split by the light spitting means to a position in front of the left and right eyes of a first observer who is squarely facing the object of observation via the Fresnel concave mirror panel, so that the parallax direction of the two images of the object of observation and the parallax direction of the first observer squarely facing the object of observation coincide, and guiding the other of the lights representing the three-dimensional image split by the light splitting means to a position in front of the left and right eyes of a second observer positioned squarely facing the object of observation from a direction different than the first observer via the Fresnel concave mirror panel, so that the parallax direction of the two images of the object of observation and the parallax direction of the second observer coincide.

* * * * *